United States Patent
Maloney

(10) Patent No.: US 8,506,589 B2
(45) Date of Patent: Aug. 13, 2013

(54) NASOGASTRIC TUBE FOR USE DURING AN ABLATION PROCEDURE

(76) Inventor: James D. Maloney, South Russell, OH (US)

(*) Notice: Subject to any disclaimer, the term of this patent is extended or adjusted under 35 U.S.C. 154(b) by 1356 days.

(21) Appl. No.: 11/932,196

(22) Filed: Oct. 31, 2007

(65) Prior Publication Data

US 2009/0112248 A1    Apr. 30, 2009

(51) Int. Cl.
*A61M 29/00* (2006.01)
*A61M 31/00* (2006.01)
*A61M 37/00* (2006.01)

(52) U.S. Cl.
USPC ............... 606/191; 604/95.04; 604/105

(58) Field of Classification Search
USPC ........... 604/95.01, 95.04, 104–109, 95.02, 604/95.03, 95.05; 600/380; 606/191, 196; 607/124
See application file for complete search history.

(56) References Cited

U.S. PATENT DOCUMENTS

| | | | |
|---|---|---|---|
| 4,180,076 A | 12/1979 | Betancourt | |
| 4,214,593 A | 7/1980 | Imbruce et al. | |
| 4,327,720 A | 5/1982 | Bronson et al. | |
| 4,785,822 A | 11/1988 | Wallace | |
| 4,920,980 A | 5/1990 | Jackowski | |
| 5,088,979 A | 2/1992 | Filip et al. | |
| 5,170,803 A | 12/1992 | Hewson et al. | |
| 5,197,963 A | 3/1993 | Parins | |
| 5,235,970 A | 8/1993 | Augustine | |
| 5,531,776 A | 7/1996 | Ward et al. | |
| 5,558,665 A * | 9/1996 | Kieturakis | 606/1 |
| 5,740,808 A | 4/1998 | Panescu et al. | |
| 5,876,448 A | 3/1999 | Thompson et al. | |
| 6,259,938 B1 | 7/2001 | Zarychta et al. | |
| 6,305,436 B1 | 10/2001 | Andersen et al. | |
| 6,508,789 B1 * | 1/2003 | Sinnott et al. | 604/164.02 |
| 6,562,031 B2 | 5/2003 | Chandrasekaran et al. | |
| 6,615,071 B1 | 9/2003 | Casscells, III et al. | |
| 6,640,120 B1 | 10/2003 | Swanson et al. | |
| 6,692,492 B2 | 2/2004 | Simpson et al. | |
| 6,712,771 B2 | 3/2004 | Haddock et al. | |
| 7,155,270 B2 | 12/2006 | Solis et al. | |
| 7,163,537 B2 | 1/2007 | Lee et al. | |

(Continued)

FOREIGN PATENT DOCUMENTS

EP        1 832 307 A1    9/2007
WO    WO 2005113057 A1 *  12/2005

OTHER PUBLICATIONS

Jihn Han, et al., "Esophageal Migration During Left Atrial Catheter Ablation for Atrial Fibrillation," *Circulation*, 2004; 110, p. 528.

(Continued)

*Primary Examiner* — Nicholas Lucchesi
*Assistant Examiner* — Nathan R Price
(74) *Attorney, Agent, or Firm* — Alston & Bird LLP

(57) ABSTRACT

Embodiments of the present invention provide a nastogastric tube for deflecting an esophagus during an ablation procedure. According to one embodiment, the nasogastric tube includes a tube comprising at least one lumen having proximal and distal ends, and an esophageal deflector positioned within the at least one lumen and configured to deflect a portion of the tube between the proximal and distal ends. The esophageal deflector is configured to deflect the portion of the tube proximate to a retrocardiac portion of the esophagus such that the retrocardiac portion of the esophagus is deflected away from an ablation site.

25 Claims, 6 Drawing Sheets

(56) References Cited

U.S. PATENT DOCUMENTS

| | | | |
|---|---|---|---|
| 7,621,908 B2 | 11/2009 | Miller | |
| 7,654,980 B2* | 2/2010 | Weststrate et al. | 604/107 |
| 7,899,555 B2* | 3/2011 | Morgan et al. | 607/130 |
| 8,133,220 B2 | 3/2012 | Lee et al. | |
| 8,224,422 B2 | 7/2012 | Mottola et al. | |
| 8,256,428 B2 | 9/2012 | Hindricks et al. | |
| 8,271,095 B2 | 9/2012 | O'Sullivan | |
| 8,273,016 B2 | 9/2012 | O'Sullivan | |
| 8,355,801 B2 | 1/2013 | O'Sullivan | |
| 2001/0012934 A1 | 8/2001 | Chandrasekaran et al. | |
| 2002/0188276 A1* | 12/2002 | Evans et al. | 604/509 |
| 2004/0243121 A1 | 12/2004 | Lee et al. | |
| 2005/0015082 A1 | 1/2005 | O'Sullivan | |
| 2005/0090729 A1 | 4/2005 | Solis | |
| 2005/0197623 A1* | 9/2005 | Leeflang et al. | 604/95.04 |
| 2006/0111707 A1 | 5/2006 | O'Sullivan | |
| 2006/0252993 A1* | 11/2006 | Freed et al. | 600/146 |
| 2007/0118105 A1 | 5/2007 | Miller | |
| 2007/0135810 A1 | 6/2007 | Lee | |
| 2007/0225701 A1 | 9/2007 | O'Sullivan | |
| 2010/0145178 A1* | 6/2010 | Kartush | 600/380 |
| 2011/0034936 A1 | 2/2011 | Maloney | |

OTHER PUBLICATIONS

Jennifer E. Cummings, et al., "Assessment of Temperature, Proximity, and Course of the Esophagus During Radiofrequency Ablation Within the Left Atrium," *Circulation*, Jul. 18, 2005, pp. 459-464.

Hsuan-Ming Tsao, et al., "Anatomic Relationship of the Esophagus and Left Atrium: Implication for Catheter Ablation of Atrial Fibrillation," *CHEST*, Oct. 2005; 128; 4; pp. 2581-2587.

Kristina Lemola, et al., "Computed Tomographic Analysis of the Anatomy of the Left Atrium and the Esophagus. Implications for Left Atrial Catheter Ablation," *Circulation*, Nov. 29, 2004, pp. 3655-3660.

Jennifer E. Cummings, et al., "Brief Communication: Atrial-Esophageal Fistulas after Radiofrequency Ablation," *Annals of Internal Medicine*, 2006; 144; pp. 572-574.

A. Marc Gillinov, et al., "Esophageal Injury During Radiofrequency Ablation for Atrial Fibrillation," *The Journal of Thoracic and Cardiovascular Surgery*, vol. 122, No. 6, Dec. 2001, pp. 1239-1240.

Heike Aupperle, et al., "Ablation of Atrial Fibrillation and Esophageal Injury: Effects of Energy Source and Ablation Technique," *The Journal of Thoracic and Cardiovascular Surgery*, vol. 130, No. 6, Dec. 2005, pp. 1549-1554.

Christian Perzanowski, et al., "Real-Time Monitoring of Luminal Esophageal Temperature During Left Atrial Radiofrequency Catheter Ablation for Atrial Fibrillation: Observations About Esophageal Heating During Ablation at the Pulmonary Vein Ostia and Posterior Left Atrium," *Journal of Cardiovascular Electrophysiology*, vol. 17, Issue 2, Feb. 2006, pp. 166-170.

Stefano Benussi, et al., "A Tailored Anatomical Approach to Prevent Complications During Left Atrial Ablation," *The Annals of Thoracic Surgery*, Jun. 2003, vol. 75, pp. 1979-1981.

Jian-Fang Ren, et al., "Esophageal Imaging and Strategies for Avoiding Injury During Left Atrial Ablation for Atrial Fibrillation," *Heart Rhythm*, vol. 3, No. 10, Oct. 2006, pp. 1156-1161.

Enrique J. Berjano, et al., "A Cooled Intraesophageal Balloon to Prevent Thermal Injury During Endocardial Surgical Radiofrequency Ablation of the Left Atrium: a Finite Element Study," *Physics in Medicine and Biology*, Oct. 21, 2005, vol. 50, No. 20, pp. N269-N279.

Scott J. Pollak, et al., "Novel Imaging Techniques of the Esophagus Enhancing Safety of Left Atrial Ablation," *Journal of Cardiovascular Electrophysiology*, vol. 16, No. 3, Mar. 2005, pp. 244-248.

Bengt Herweg, et al., "Mechanical Esophageal Deflection During Ablation of Atrial Fibrillation," *Pacing and Clinical Electrophysiology*, Sep. 2006, vol. 29, Issue 9, pp. 957-961.

"Imaging Technique May Prevent Injury During Ablation for Atrial Fibrillation," Physorg.com <http://www.physorg.com/printnews.php?newsid=75471025>, published Aug. 22, 2006.

Jeff Minerd, "Echo Safeguards Esophagus During RF Ablation for Afib," MedPageToday.com, <http://www.medpagetoday.com/tbprint.cfm?tbid=3998&topicid=96>, published Aug. 25, 2006.

"Injury During Ablation for Atrial Fibrillation may be Prevented by Imaging Technique," RadiologyToday.net, <http://www.radiologytoday.net/rtdaily8302006.shtml>, printed Oct. 16, 2006.

Sujoya Dey, et al., "Esophageal Diverticulum Illustrated by Barium Swallow During Left Atrial Catheter Ablation for Atrial Fibrillation," *Circulation*, vol. 114, No. 21, Nov. 2006, p. e597.

Mauricio I. Scanavacca, et al., "Left Atrial-Esophageal Fistula Following Radiofrequency Catheter Ablation of Atrial Fibrillation," *Journal of Cardiovascular Electrophysiology*, vol. 15, No. 8, Aug. 2004, pp. 960-962.

Eric Good, et al., "Movement of the Esophagus During Left Atrial Catheter Ablation for Atrial Fibrillation," *Journal of the American College of Cardiology*, vol. 46, No. 11, Dec. 2005, pp. 2107-2110.

T. Jared Bunch, et al., "Temporary Esophageal Stenting Allows Healing of Esophageal Perforations Following Atrial Fibrillation Ablation Procedures," *Journal of Cardiovascular Electrophysiology*, vol. 17, No. 4, Apr. 2006, pp. 435-439.

International Search Report and Written Opinion for International Application No. PCT/US2011/056886, mailed Jan. 5, 2012.

Office Action for U.S. Appl. No. 12/909,195, filed Jan. 23, 2013.

\* cited by examiner

NASOGASTRIC TUBE FOR USE DURING AN ABLATION PROCEDURE

FIELD OF THE INVENTION

Embodiments of the present invention relate generally to a nasogastric tube and, more particularly, to a nasogastric tube for deflecting the esophagus and monitoring various properties of the esophagus during an ablation procedure.

BACKGROUND OF THE INVENTION

Esophageal tubes, probes, balloons, and other devices have been used to monitor internal physiologic function, decompress all portions of the alimentary tract, and protect the airway in sedated patients undergoing surgical procedures. It is currently common medical practice to use a nasogastric tube in most patients requiring mechanical ventilation during surgical procedures, and to use a nasogastric tube to mark the anatomic relationships between the left atrium and the esophagus in patients undergoing atrial fibrillation ablation with general anesthesia and or conscious sedation procedures. Marking the esophagus during atrial fibrillation (left atrial) ablation has gained prominence because of the occurrence of unintended esophageal heat injury.

Various ablation techniques, such as high-energy microwaves, radiofrequency, and cryogenic methods, have been used to create a focal tissue lesion in the atrium to treat atrial disrhythmias or atrial fibrillation. Common left atrial ablation techniques include wide circumferential lesions encircling the pulmonary veins and linear lesions on the posterior left atrium, mitral isthmus, and left atrium roof. The esophagus and posterior left atrial wall are located proximate to one another (see FIG. 1) and near the ablation zone for left atrial ablation and pulmonary vein isolation. Studies have shown that the mean length and width of the esophagus in contact with the posterior left atrium are 5.8 centimeters and 1.36 centimeters, respectively. Although most patients have a small fat pad separating the posterior left atrium and esophagus, this fat pad is often discontinuous. Due to the close proximity of the esophagus and the left atrium, ablation along the posterior left atrium may result in unintended thermal injury to the esophagus and subsequent fatal esophageal-atrial fistula presenting as a fatal complication 1-3 weeks following left atrial ablation. An esophageal-atrial fistula can cause an air embolism with a stroke, mediastinitis, or GI bleeding having high mortality rates.

Different techniques have been used to monitor the temperature and position of the esophagus during ablation of the atrium. Strategies to avoid esophageal injury resulting from left atrial ablation include: avoidance of energy delivery at close esophageal atrial sites, decreased ablative energy and duration of energy delivery (time) at target sites, use of intracardiac echo and other imaging techniques to avoid unsafe ablative sites, and esophageal temperature monitoring to recognize esophageal heating. However, these precautionary approaches have proven to be unreliable and/or likely to compromise the ablation procedure.

The anterior wall of the esophagus is separated from the posterior wall of the left atrium and/or the proximal pulmonary vein by 0 to 4 millimeters of fat and the oblique sinus recess of the pericardium. The separation distance between the anterior wall of the esophagus and the posterior wall of the left atrium becomes even less during phases of peristalsis of the esophageal musculature. The esophagus is a mobile organ that allows peristalic movement and adjusts to thoracic and diaphragmatic motion. Esophageal mobility is limited to some degree by venous connections and drainage of the esophagus, azyis vein and anchoring to the posterior mediastinal connective tissue. As a result, static imaging techniques may be inadequate to monitor the position of the esophagus due to the mobility of the esophagus. Thus, real-time imaging techniques, such as intracardiac echocardiography, may be more effective in monitoring the variable esophageal and left atrial anatomic relationship due to mobility and peristalsis of the esophagus.

An alternative approach to avoid injury to the esophagus has been to deflect the esophagus away from the ablation site, such as by moving the esophagus one centimeter or more from the ablation site. Transesophageal echo probes have been utilized in attempts to deflect or mobilize the retrocardiac portion of the esophagus away from ablation sites, but have had limited success due to the bulkiness of the device and the inability of the curved distal tip of the probe to effectively deflect the esophagus. Attempts to excessively mobilize the esophagus need to be avoided, but gentle intraluminal deflection of 0.5 to 3.0 cm is within the physiologic range.

Therefore, there is a need for a nasogastric tube for deflecting the esophagus to reduce the incidence of thermal injury of the esophagus due to an ablation procedure. In addition, there is a need for techniques to monitor the esophagus during an ablation procedure to avoid thermal injury to the esophagus.

SUMMARY OF THE INVENTION

Embodiments of the present invention provide a nasogastric tube and method of using the same for deflecting an esophagus during an ablation procedure, such as left atrial ablation for treating atrial fibrillation. The nasogastric tube includes one or more lumens for receiving an esophageal deflector that is configured to deflect the esophagus away from the ablation site and within the physiological range during an ablation procedure so as to reduce the incidence of thermal injury to the esophagus. Furthermore, embodiments of the present invention provide a nasogastric tube that includes a plurality of lumens that are configured to receive one or more instruments to monitor the position and/or physical properties of the esophagus during an ablation procedure, as well as assist in positioning the nasogastric tube in the esophagus. Visualizing and monitoring various properties of the target area during ablation can provide a technique to avoid thermal esophageal injury.

According to one embodiment, the nasogastric tube includes a tube comprising at least one lumen having proximal and distal ends, and an esophageal deflector (e.g., a pull-wire apparatus) positioned within the lumen and configured to deflect a portion of the tube between the proximal and distal ends. The esophageal deflector is configured to deflect the portion of the tube proximate to a retrocardiac portion of the esophagus such that the retrocardiac portion of the esophagus is deflected away from an ablation site. For example, the esophageal deflector may be configured to deflect the retrocardiac portion of the esophagus during a left atrium ablation procedure and/or deflect the retrocardiac portion of the esophagus laterally or posteriorly.

Aspects of the nasogastric tube include a nasogastric tube having a plurality of lumens. Each of the plurality of lumens may be configured to receive a pressure transducer, a temperature recorder, an electrogram recorder, an electroanatomic positioning apparatus, a balloon, a guide wire, and/or a syringe. According to one embodiment, one of the lumens is configured to receive an expandable basket. The expandable basket may include a plurality of thermisters and a plurality of electrodes. In addition, the nasogastric tube may include an opening between its proximal and distal ends, wherein at least a portion of the basket is configured to expand out of the opening and proximate or adjacent to the esophagus. Additional aspects include a nasogastric tube comprising an elastomeric material. The esophageal deflector may be configured to deflect the tube along a length of about 4 to 10 cm and/or to deflect a portion of the tube to a radius of about 0.5 to 4 cm. Moreover, at least a portion of the esophageal deflector may be fluoroscopically visible.

Another embodiment of the present invention provides a nasogastric tube having a tube comprising a plurality of lumens each having proximal and distal ends. The nasogastric tube also includes an esophageal deflector positioned within one of the plurality of lumens and configured to deflect a portion of the tube between the proximal and distal ends. In addition, the nasogastric tube includes at least one instrument positioned within one of the plurality of lumens and configured to monitor the position of the esophagus during an ablation procedure, monitor one or more physical properties of the esophagus during an ablation procedure, and/or assist in positioning the tube within the esophagus.

Moreover, one embodiment of the present invention provides a method for deflecting the esophagus during an ablation procedure. The method includes inserting a nasogastric tube into the esophagus, wherein the nasogastric tube comprises at least one lumen having proximal and distal ends and an esophageal deflector positioned within the at least one lumen. The method further includes actuating the esophageal deflector so as to deflect a portion of the tube between the proximal and distal ends and proximate to a retrocardiac portion of the esophagus such that the retrocardiac portion of the esophagus is deflected away from an ablation site.

Various aspects of the method include inserting a nasogastric tube having a plurality of lumens into the esophagus. The method may further include inserting an expandable basket, a pressure transducer, a temperature recorder, an electrogram recorder, an electroanatomic positioning apparatus, a balloon, a guide wire, and/or a syringe into one of the plurality of lumens. Furthermore, the deflecting step may include deflecting the retrocardiac portion of the esophagus during a left atrium ablation procedure and/or deflecting the retrocardiac portion of the esophagus laterally or posteriorly. The inserting step could include inserting the nasogastric tube such that the nasogastric tube extends from a proximal end of the esophagus to a distal end of the esophagus or a gastric fundus.

BRIEF DESCRIPTION OF THE DRAWINGS

Figure 1:
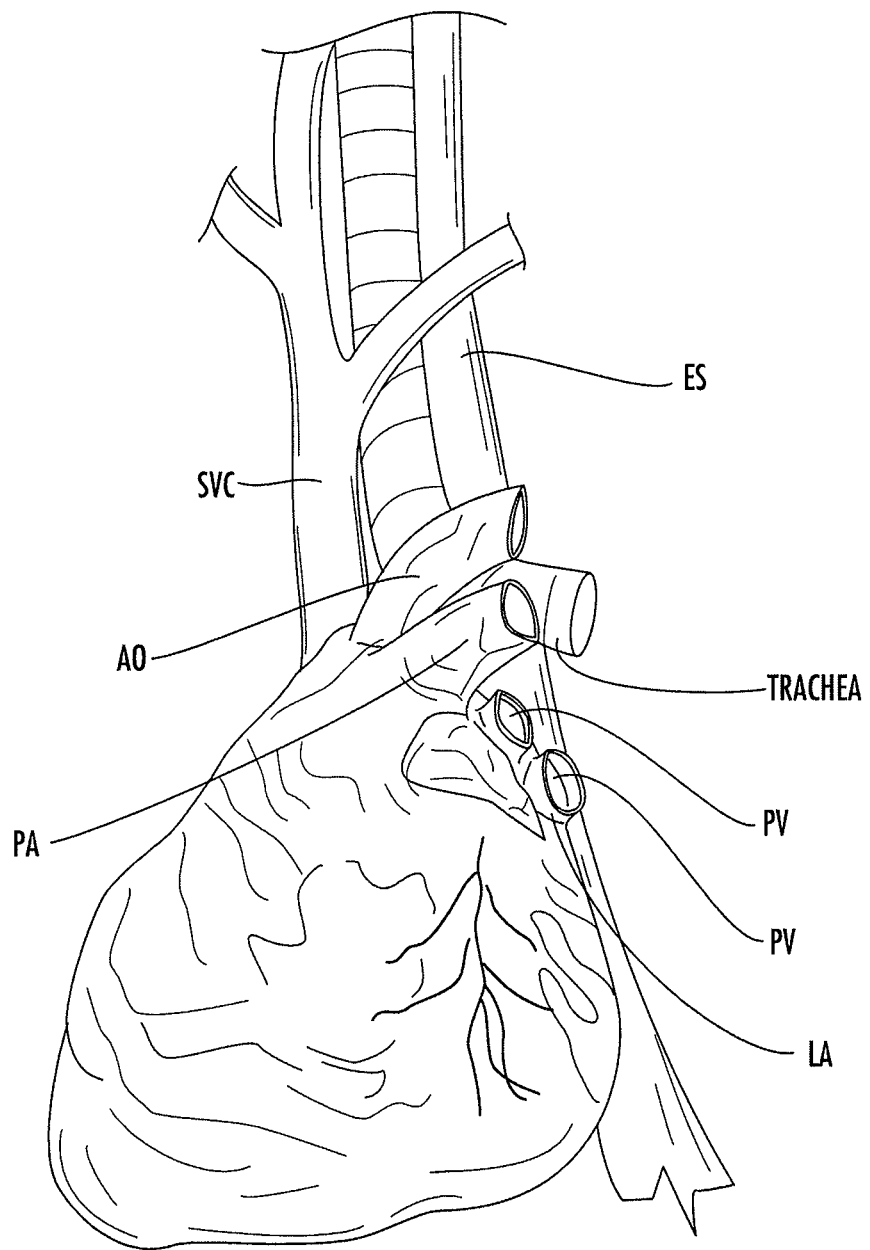
Figure 2:
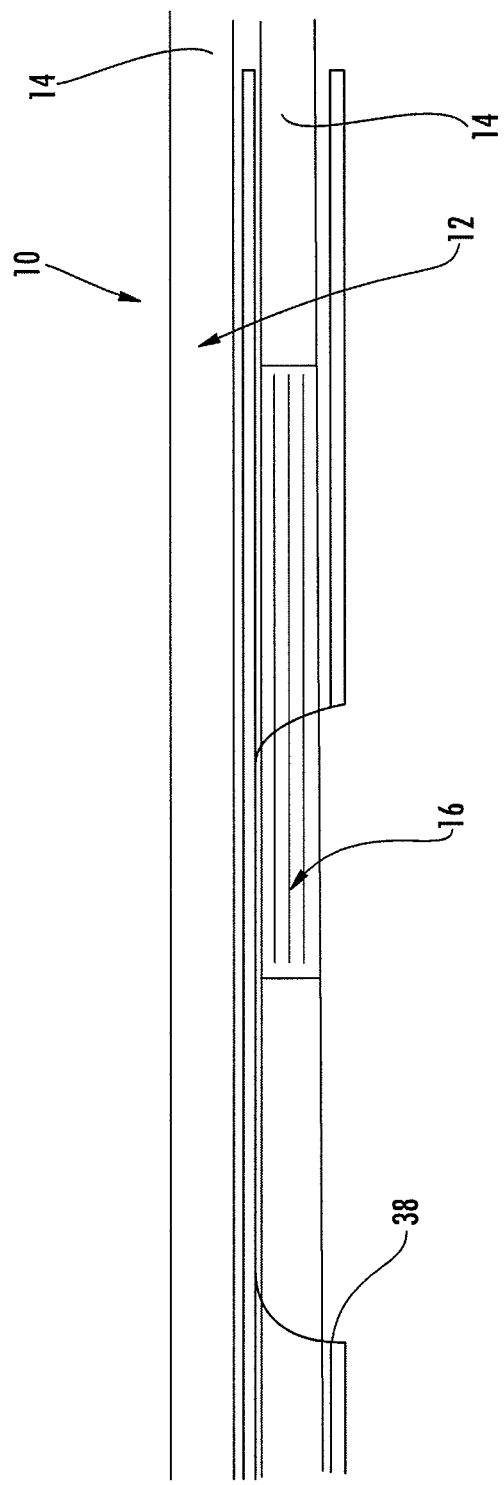
Figure 3:
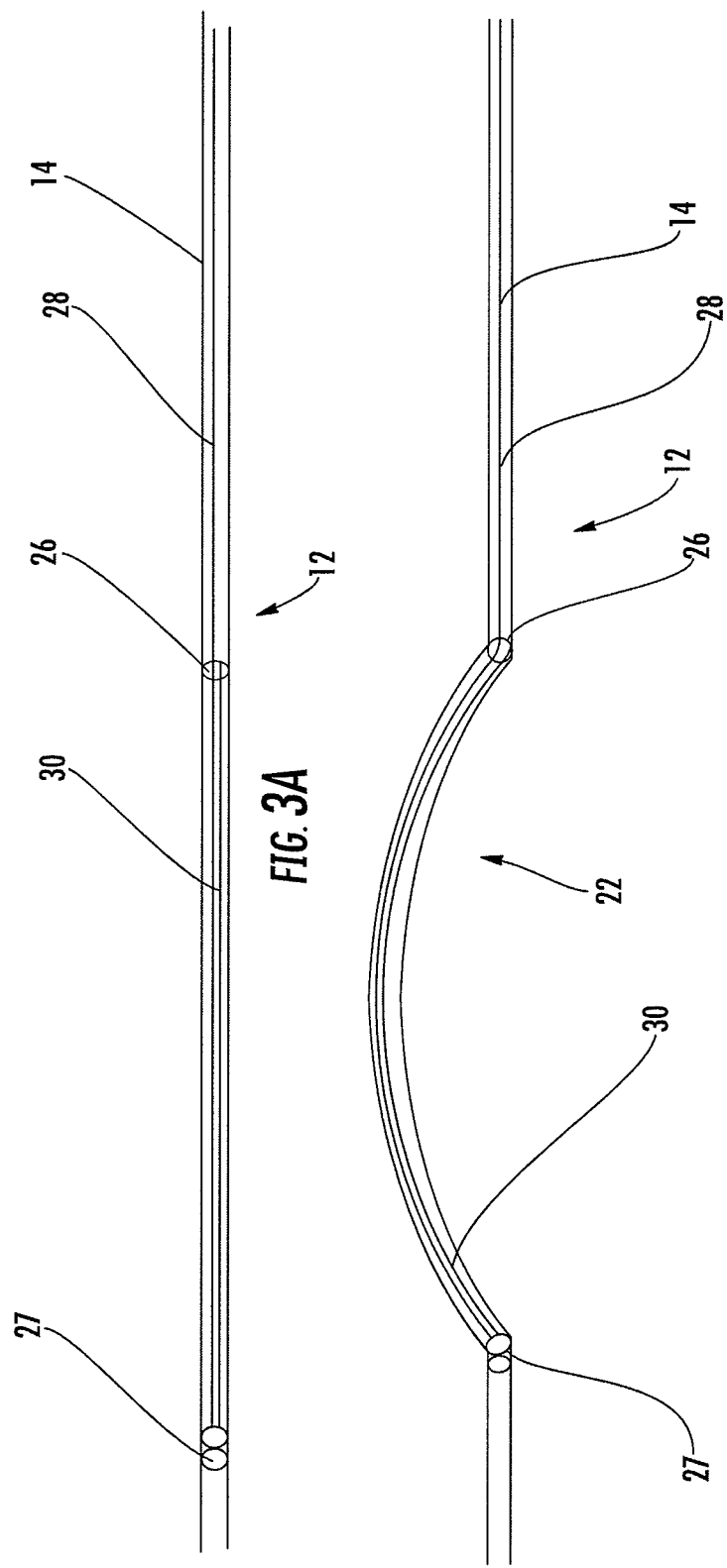
Figure 4:
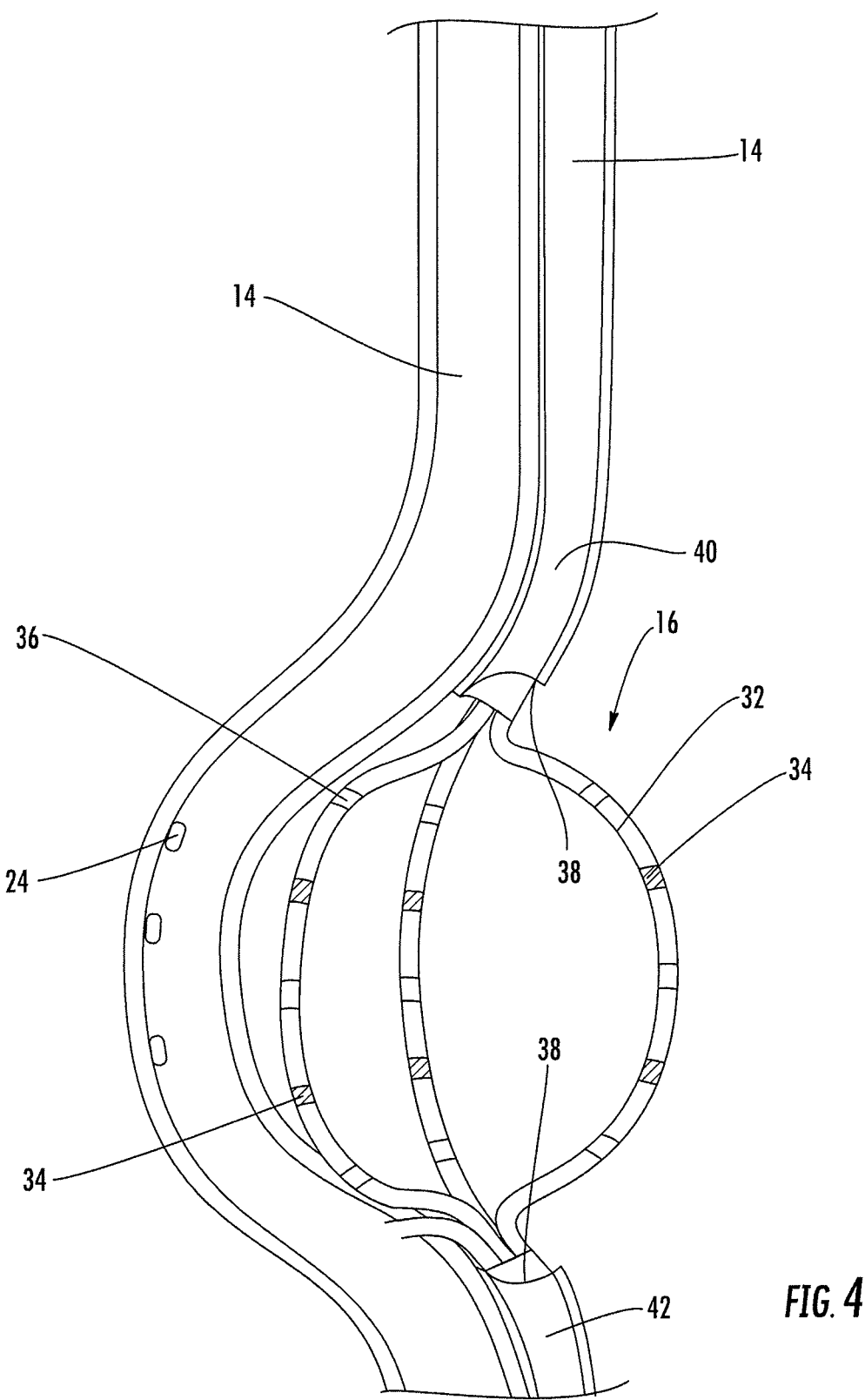
Figure 5A:
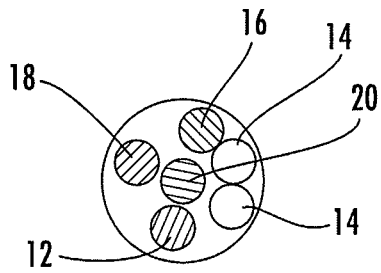
Figure 5B:
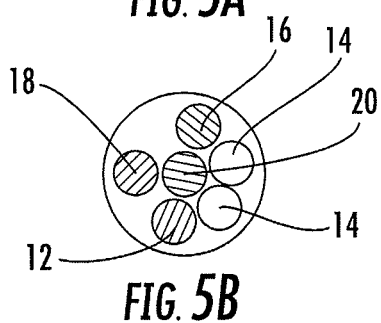
Figure 5C:
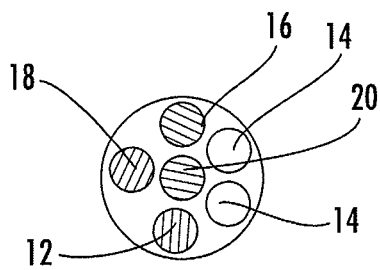
Figure 5D:
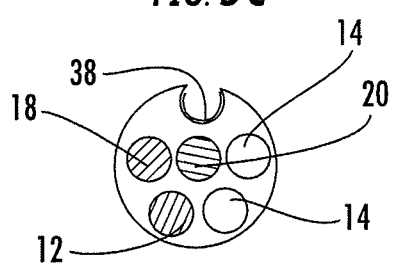
Figure 5E:
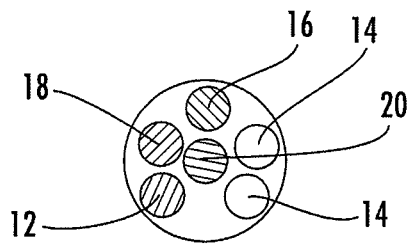
Figure 6:
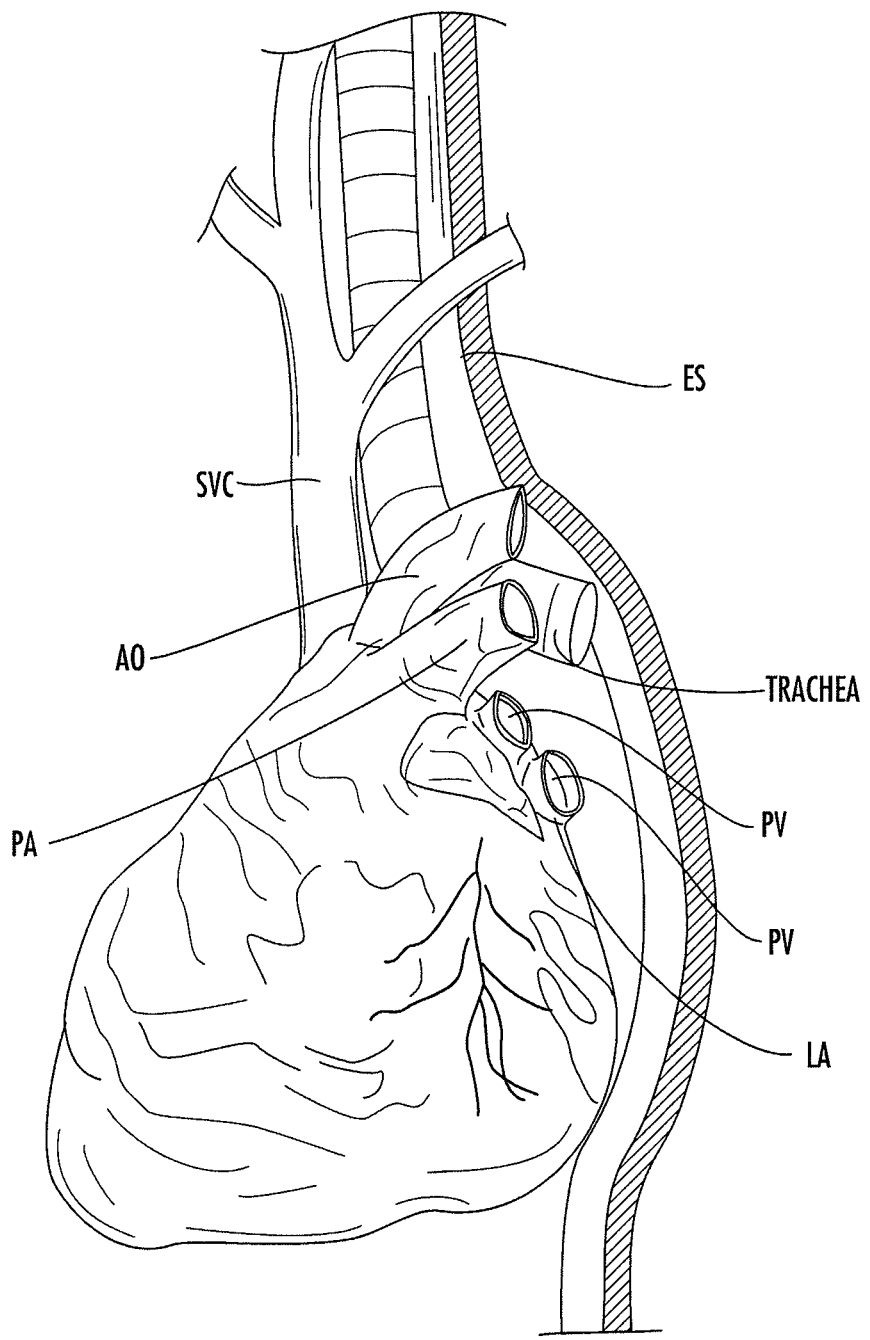

Having thus described various embodiments of the invention in general terms, reference will now be made to the accompanying drawings, which are not necessarily drawn to scale, and wherein:

FIG. 1 shows a lateral view of the anatomic arrangement of the esophagus, heart, and pulmonary veins with respect to one another;

FIG. 2 illustrates a side view of a nasogastric tube according to one embodiment of the present invention;

FIGS. 3A-3B depict an esophageal deflector according to one embodiment of the present invention;

FIG. 4 illustrates an expandable basket according to an embodiment of the present invention;

FIGS. 5A-5E show cross-sectional views of the nasogastric tube shown in FIG. 1; and FIG. 6 illustrates a nasogastric tube deflecting the esophagus according to one embodiment of the present invention.

DETAILED DESCRIPTION

The present inventions now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Referring to FIG. 2, there is shown a nasogastric tube 10 according to one embodiment of the present invention. In general, the nasogastric tube 10 includes at least one lumen 14 for receiving an instrument therein. According to one embodiment, an esophageal deflector 12 is positioned within the lumen 14 and is configured to deflect the esophagus during an ablation procedure. For example, the esophageal deflector 12 may be configured to deflect a portion of the nasogastric tube 10 proximate to a retrocardiac portion of the esophagus such that the retrocardiac portion of the esophagus is deflected away from an ablation site. Deflecting the esophagus away from the ablation site may reduce the incidence of thermal injury of the esophagus during ablation procedures, such as left atrial ablation.

Although the term "nasogastric" is used herein as describing a nasogastric tube 10 that is configured to be inserted through the nose or throat into the esophagus during an ablation procedure, it is understood that the nasogastric tube could be positioned within various body cavities for displacing a portion of the anatomy. Moreover, the nasogastric tube 10 may be a variety of materials, such as a polymeric material (e.g., polyurethane). According to one embodiment, the nasogastric tube 10 is a flexible elastomeric material, such as silicone. In addition, the nasogastric tube 10 may be a variety of sizes and configurations depending on its use. For example, the outer diameter of the nasogastric tube 10 may be about 5-10 mm, and/or the nasogastric tube could have a tapered atraumatic tip. The nasogastric tube 10 may also be various lengths and may, for example, extend from the nose or throat and caudally to the distal esophagus and/or gastric fundus.

FIGS. 2 and 5A-5E illustrate that the nasogastric tube 10 includes a plurality of lumens 14 (e.g., six lumens), although a single lumen could be used if desired. According to one embodiment, a central tube includes a plurality of smaller tubes slidably or securely positioned therein that define respective lumens 14. Alternatively, the central tube could have a plurality of lumens 14 defined therein, such as by integrally forming the lumens via molding. Each lumen 14 is configured to receive one or more instruments therein. The instruments could be used to monitor the position and/or physical properties of the esophagus during an ablation procedure, as well as assist in positioning the nasogastric tube 10 in the esophagus. Various instruments could be inserted within the lumens 14, such as a pressure transducer, a temperature recorder, an electrogram recorder, an electroanatomic positioning apparatus, a balloon, a guide wire, or a syringe. For example, monitoring instruments may be used for fluoroscopic visualization, adjacent wall temperature monitoring, intraesophageal temperature mapping, magnetic and/or electroanatomic 3D mapping, cardiac electrogram pacing and recording, and the like, of the esophagus, such as the retrocardiac portion of the esophagus. According to one embodiment, the nasogastric tube 10 is configured to receive a pressure transducer in one of the lumens 14 that includes a semi-conductor chip having a piezoresistive pressure diaphragm that facilitates monitoring of pressure applied to the esophagus, such as pressure applied when deflecting the retrocardiac portion of the esophagus, as explained in further detail below. Also, one or more of the lumens 14 can be used for providing and/or removing fluids and may be connected to a syringe suction/infusion device. Moreover, one or more of the lumens 14 could be left open such that different instruments may be inserted and removed from the lumens during an ablation procedure.

According to one embodiment, one of the lumens 14 is configured to receive a guide wire 18 to facilitate nasal-oral passage of the nasogastric tube 10 into the esophagus. For example, the guide wire 18 could be inserted through the nose or throat and into the esophagus and passed caudally to the distal esophagus and/or gastric fundus so as to facilitate placement of the nasogastric tube 10 in the esophagus. The guide wire 18 could be guided via fluoroscopy and/or by feel. The guide wire 18 could be removable and may extend from the proximal end of the nasogastric tube 10 and distally of the distal end of the nasogastric tube. In addition, the guide wire 18 is typically flexible and may be manually curved and/or deflectable using a pull-wire mechanism.

A lumen 14 of the nasogastric tube 10 may also be configured to receive an inflatable balloon 20. In particular, the inflatable balloon 20 may be positioned proximate to a distal end of the nasogastric tube 10 so that the balloon may be expanded to fix the nasogastric tube in position. In particular, the inflatable balloon 20 may be inflated to fix or tether the nasogastric tube 10 on the gastric side of the gastro-esophageal sphincter to provide additional stability and facilitate deflection of the esophagus and reduce or eliminate esophageal reflux thereby decreasing the potential for aspiration.

Furthermore, one of the lumens 14 is configured to receive an esophageal deflector 12, as shown in FIGS. 2 and 3A-3B. The esophageal deflector 12 is configured to deflect a portion of the tube between the proximal and distal ends. For example, the esophageal deflector 12 may be configured to create a gentle C-shaped curve of a portion of the nasogastric tube 10. In addition, the esophageal deflector 12 is configured to deflect the tube along a length of about 4 to 10 cm and to a radius of about 0.5 to 4 cm, although the esophageal deflector is capable of deflecting the nasogastric tube along various lengths and to various radii if desired.

According to one embodiment, the esophageal deflector 12 is configured to deflect a portion of the nasogastric tube 10 proximate to a retrocardiac portion of the esophagus such that the retrocardiac portion of the esophagus may be deflected away from an ablation site, such as during a left atrium ablation procedure. For example, the esophageal deflector 12 could be used to deflect the nasogastric tube 10 in order to apply pressure to the posterior and posterior lateral internal esophageal wall thereby pulling the anterior and anteriolateral wall of the esophagus away from the posterior left atrial ablation site (see FIG. 6). According to one embodiment, the esophageal deflector 12 is configured to separate the anterior wall of the esophagus about 3 to 8 mm from the posterior left atrial ablation site. Furthermore, the nasogastric tube 10 and/or esophageal deflector 12 may be rotated so that the curved pressure applied to the retrocardiac portion of the esophagus may be deflected in any direction from the left-atrial, left-ventricle sites. In other words, the esophagus may be moved posterior, posterior right lateral, or posterior left lateral in relationship to the position of an intracardiac ablation electrode.

Moreover, at least a portion of the nasogastric tube 10 and/or esophageal deflector 12 may be fluoroscopically visible in order to facilitate positioning within the esophagus. In addition, the nasogastric tube 10 and/or esophageal deflector 12 may include one or more radiopaque markers 24 that facilitate radiographic and/or electroanatomic positioning and/or deflection of the esophagus. The nasogastric tube 10 and/or esophageal deflector 12 may include one or more thermisters for measuring and/or monitoring temperature changes and localizing the position of the electrode used in an ablation procedure in relation to the ablation site (e.g., left atrium).

According to one embodiment of the present invention, the esophageal deflector 12 includes a pull-wire apparatus 22. The pull wire apparatus 22 may be integrated into the nasogastric tube 10 or one of the lumens 14 within the nasogastric tube and is configured to deflect a portion of the nasogastric tube, such as into a C-shaped curve. For example, FIG. 3A illustrates that the pull wire apparatus 22 may include a pair of rings 26, 27 coupled to first 28 and second 30 wires. In particular a first pull wire 28 extends from an actuator (not shown) or proximal end of the nasogastric tube 10 and attaches to a first ring 27, while the second pull wire 30 extends between the pair of rings 26, 27. As the actuator, such as a rotatable handle or slidable trigger, actuates the first pull wire 28 by pulling the pull wire proximally, the second pull wire 30 deflects outwardly as shown in FIG. 3B. Thus, the second pull wire 30 may be a flexible material that is capable of deflecting outwardly and is of sufficient rigidity to deflect the nasogastric tube 10 outwardly. It is understood that various pull-wire apparatus and other techniques could be used to deflect the nasogastric tube 10. For example, the esophageal deflector 12 could include a single wire that may be pushed distally within the lumen 14 and then bow outwardly at its distal end or that is a semi-rigid bent wire.

FIGS. 2 and 4 show that the nasogastric tube 10 is configured to receive an expandable basket 16. The expandable basket 16 includes a plurality of flexible arms 32 having respective thermisters 34 and electrodes 36. For example, there may be 3-5 flexible arms 32, although any number of arms could be used to provide three-dimensional expansion. The flexible arms 32 are fixed at their proximal ends with a proximal tube 40 and fixed at their distal ends with a distal tube 42. The proximal tube 40 is typically longer than the distal tube 42, while the distal tube may be, for example 2-4 cm in length. An opening 38 is defined in a portion of the nasogastric tube 10 between the proximal and distal ends, and at least a portion of the expandable basket 16 is configured to expand out of the opening and proximate to the esophagus. Thus, as shown in FIG. 2, the expandable basket 16 is positioned within the lumen 14 prior to being moved distally so as to expand out of the opening 38, as illustrated in FIG. 4. Thus, the flexible arms 32 may comprise a memory material that is configured to bias outwardly of the opening 38, as well as inwardly as the arms are moved proximally within the lumen 14. In addition, the amount of expansion of the expandable basket 16 may be adjusted by moving the expandable basket proximally or distally. For instance, moving the expandable basket 16 to align with the opening 38 provides full expansion, while the expandable basket may be incrementally moved proximally in order to reduce the amount of expansion. The expandable basket 16 may be deployed at various times during an ablation procedure, including when the nasogastric tube 10 is deflected.

The lumen 14 for receiving the expandable basket 16 may be positioned in the cephlad extra oral portion of the nasogastric tube 10. The opening 38 may be defined proximate to the portion of the tube that may be deflected in the retrocardiac portion of the esophagus, such as just below the tracheal bifurcation and extending 5-8 cm. Thus, the flexible arms 32 are configured to bias outwardly to contact the esophageal wall, but preferably do not independently deflect or expand the esophagus. There may be any number of thermisters 34 per flexible arm 32 (e.g., 3-9) in order to obtain circumferential temperature measurements. Furthermore, there may be any number of electrodes 36 (e.g., 4-10) that are configured to provide electrogram and/or positional measurements. Thus, the expandable basket 16 may provide various measurements simultaneously, as well as concurrently with similar measurements obtained within the atrium or ventricle via intracardiac monitoring. Moreover, the expandable basket 16 may be used during an ablation procedure, such as left atrial ablation, so that the temperature and position of the esophagus may be monitored in order to reduce the incidence of thermal injury to the esophagus. For example, if the temperature of the esophagus is approaching a dangerous level, the power to the electrode may be reduced or the esophagus further deflected or moved to avoid thermal injury to the esophagus.

During use according to one embodiment of the present invention, a physician inserts a nasogastric tube 10 into the esophagus, typically via the nose or throat. The physician could utilize a guide wire 18 to facilitate insertion of the nasogastric tube 10 within the esophagus. The nasogastric tube 10 could be inserted such that the nasogastric tube extends from a proximal end of the esophagus to a distal end of the esophagus or a gastric fundus. The distal end of the nasogastric tube 10 could be anchored via an inflatable balloon for further stabilization. Once properly positioned within the esophagus, the physician may actuate the esophageal deflector 12 so as to deflect a portion of the nasogastric tube 10 between the proximal and distal ends and proximate to a retrocardiac portion of the esophagus such that the retrocardiac portion of the esophagus is deflected away from an ablation site. The physician may also employ various other instruments while the esophagus is deflected or non-deflected, such as expandable basket 16, a pressure transducer, a temperature recorder, an electrogram recorder, an electroanatomic positioning apparatus, a balloon, a guide wire, and/or a syringe. The esophageal deflector 12 is configured to deflect the retrocardiac portion of the esophagus during a left atrium ablation procedure, as well as deflect the retrocardiac portion of the esophagus laterally or posteriorly while an ablation procedure is being performed. For instance, the esophageal deflector 12 could deflect the esophagus away from the ablation electrode during an ablation procedure.

Therefore, embodiments of the present invention may provide several advantages. For example, one embodiment of the present invention provides a nasogastric tube 10 that is configured to deflect the esophagus during an ablation procedure, such as left atrial ablation, thereby reducing the potential for thermal injury to the esophagus. The nasogastric tube 10 includes an esophageal deflector 12 that is configured to deflect the retrocardiac portion of the esophagus, which is proximate to the posterior left atrial wall and susceptible to thermal injury during an ablation procedure. A physician is also able to manipulate the nasogastric tube 10 in response to peristaltic movement of the esophagus and while performing an ablation procedure. The nasogastric tube 10 may also include one or more lumens 14 for receiving various instruments to monitor the position and/or physical properties of the esophagus during an ablation procedure, as well as assist in positioning the nasogastric tube in the esophagus, which provides additional safeguards to avoid injury to the esophagus, as well as assist the physician during an ablation procedure.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A nasogastric tube for deflecting an esophagus during an ablation procedure comprising:
   a tube comprising at least one lumen having proximal and distal ends, the tube configured to be positioned within the esophagus, to extend at least from a proximal end of the esophagus to a distal end of the esophagus, and to be anchored within the esophagus; and
   an esophageal deflector positioned within the at least one lumen and configured to deflect a portion of the tube between the proximal and distal ends, the esophageal deflector including a proximal portion, a distal portion, and an intermediate portion disposed between the proximal and distal portions, the proximal portion, the distal portion, and the intermediate portion extending along a longitudinal axis in an initial non-deflected state, the intermediate portion having a proximal end and a distal end each spaced away from the proximal end and the distal end of the tube, respectively, the proximal portion extending between the proximal end of the tube and the proximal end of the intermediate portion and the distal portion extending between the distal end of the tube and the distal end of the intermediate portion,
   wherein the esophageal deflector is configured to deflect the tube from the initial non-deflected state to a deflected state whereby the intermediate portion is deflected away from the longitudinal axis without deflecting the proximal and distal portions, and
   wherein the esophageal deflector comprises a pull-wire apparatus including a first pull wire extending from a proximal end of the nasogastric tube and anchored proximate the distal end of the intermediate portion, and a second pull wire extending between and anchored proximate the distal end of the intermediate portion and the proximal end of the intermediate portion, wherein the first pull wire is actuatable by the user and the second pull wire is configured to deflect the intermediate portion of the esophageal deflector in response to actuation of the first pull wire by the user to deflect the intermediate portion such that the tube deflects proximate to a retrocardiac portion of the esophagus while the distal end of the tube is anchored relative to the esophagus and such that the retrocardiac portion of the esophagus is deflected away from an ablation site.

2. The nasogastric tube of claim 1, wherein the tube comprises a plurality of lumens.

3. The nasogastric tube of claim 2, wherein each of the plurality of lumens is configured to receive at least one instrument selected from a group consisting of a pressure transducer, a temperature recorder, an electrogram recorder, an electroanatomic positioning apparatus, a balloon, a guide wire, or a syringe.

4. The nasogastric tube of claim 2, wherein one of the plurality of lumens is configured to receive an expandable basket.

5. The nasogastric tube of claim 4, wherein the expandable basket comprises a plurality of thermisters and a plurality of electrodes.

6. The nasogastric tube of claim 4, wherein an opening is defined in a portion of the tube between the proximal and distal ends, and wherein at least a portion of the basket is configured to expand out of the opening and proximate or adjacent to the esophagus.

7. The nasogastric tube of claim 1, wherein the tube comprises an elastomeric material.

8. The nasogastric tube of claim 1, wherein the esophageal deflector is configured to deflect the intermediate portion along a length of about 4 to 10 cm of the tube.

9. The nasogastric tube of claim 1, wherein the esophageal deflector is configured to deflect the intermediate portion such that the tube has a radius of about 0.5 to 4 cm.

10. The nasogastric tube of claim 1, wherein at least a portion of the esophageal deflector is fluoroscopically visible.

11. The nasogastric tube of claim 1, wherein the esophageal deflector is configured to deflect the retrocardiac portion of the esophagus during a left atrium ablation procedure.

12. The nasogastric tube of claim 11, wherein the esophageal deflector is configured to deflect the retrocardiac portion of the esophagus laterally or posteriorly.

13. The nasogastric tube of claim 1, further comprising an inflatable balloon at the distal end of the tube configured to be inflated to anchor the tube relative to the esophagus.

14. A method for deflecting an esophagus during an ablation procedure comprising:
  inserting the nasogastric tube of claim 1 into the esophagus; and
  actuating the esophageal deflector so as to deflect the intermediate portion such that the tube between the proximal and distal ends deflects proximate to a retrocardiac portion of the esophagus and such that the retrocardiac portion of the esophagus is deflected away from an ablation site.

15. The method of claim 14, wherein inserting comprises inserting a nasogastric tube having a plurality of lumens into the esophagus.

16. The method of claim 15, further comprising inserting at least one instrument selected from a group consisting of an expandable basket, a pressure transducer, a temperature recorder, an electrogram recorder, an electroanatomic positioning apparatus, a balloon, a guide wire, or a syringe into one of the plurality of lumens.

17. The method of claim 14, wherein deflecting comprises deflecting the retrocardiac portion of the esophagus during a left atrium ablation procedure.

18. The method of claim 14, wherein deflecting comprises deflecting the retrocardiac portion of the esophagus laterally or posteriorly.

19. The method of claim 14, wherein inserting comprises inserting the nasogastric tube such that the nasogastric tube extends from a proximal end of the esophagus to a distal end of the esophagus or a gastric fundus.

20. A nasogastric tube for deflecting an esophagus during an ablation procedure comprising:
  a tube comprising a plurality of lumens each having proximal and distal ends;
  an inflatable balloon coupled to the tube and configured to anchor the distal end of the tube relative to the esophagus;
  an esophageal deflector positioned within one of the plurality of lumens, the esophageal deflector including a proximal portion, a distal portion, and an intermediate portion disposed between the proximal and distal portions, wherein the esophageal deflector comprises a pull-wire apparatus including a first pull wire extending from the proximal end of the tube and anchored proximate a distal end of the intermediate portion, and a second pull wire extending between and anchored proximate the distal end of the intermediate portion and a proximal end of the intermediate portion, wherein the first pull wire is actuatable by the user and the second pull wire is configured to deflect the intermediate portion of the esophageal deflector in response to actuation of the first pull wire by the user to deflect the intermediate portion of the tube between the proximal and distal ends, wherein the esophageal deflector is configured to deflect the tube from an initial non-deflected state to a deflected state whereby the intermediate portion is deflected without deflecting the proximal and distal ends of the tube; and
  at least one instrument positioned within one of the plurality of lumens and configured to monitor the position of the esophagus during an ablation procedure, monitor one or more physical properties of the esophagus during an ablation procedure, and/or assist in positioning the tube within the esophagus.

21. The nasogastric tube of claim 20, wherein the esophageal deflector is configured to deflect the portion of the tube proximate to a retrocardiac portion of the esophagus such that the retrocardiac portion of the esophagus is deflected away from an ablation site.

22. The nasogastric tube of claim 20, wherein each of the plurality of lumens is configured to receive at least one instrument selected from a group consisting of a pressure transducer, a temperature recorder, an electrogram recorder, an electroanatomic positioning apparatus, a balloon, a guide wire, or a syringe.

23. The nasogastric tube of claim 20, wherein one of the plurality of lumens is configured to receive an expandable basket.

24. The nasogastric tube of claim 23, wherein the expandable basket comprises a plurality of thermisters and a plurality of electrodes.

25. The nasogastric tube of claim 23, wherein an opening is defined in a portion of the tube between the proximal and distal ends, and wherein at least a portion of the basket is configured to expand out of the opening and proximate or adjacent to the esophagus.

\* \* \* \* \*